United States Patent
Stengel et al.

(10) Patent No.: US 8,873,052 B2
(45) Date of Patent: Oct. 28, 2014

(54) METHOD AND DEVICE FOR DETERMINING THE QUALITY OF MEASUREMENT RESULTS OF A SCATTERED LIGHT METER

(75) Inventors: Karl Stengel, Deizisau (DE); Gerhard Haaga, Ohmden (DE); Michael Neuendorf, Plochingen (DE); Raymond Sieg, Esslingen (DE)

(73) Assignee: Robert Bosch GmbH, Stuttgart (DE)

( * ) Notice: Subject to any disclaimer, the term of this patent is extended or adjusted under 35 U.S.C. 154(b) by 75 days.

(21) Appl. No.: 13/581,233

(22) PCT Filed: Jan. 3, 2011

(86) PCT No.: PCT/EP2011/050031
§ 371 (c)(1),
(2), (4) Date: Nov. 16, 2012

(87) PCT Pub. No.: WO2011/104039
PCT Pub. Date: Sep. 1, 2011

(65) Prior Publication Data
US 2013/0057859 A1    Mar. 7, 2013

(30) Foreign Application Priority Data
Feb. 26, 2010  (DE) .................. 10 2010 002 420

(51) Int. Cl.
| G01N 21/00 | (2006.01) |
| G01N 21/47 | (2006.01) |
| G01N 21/53 | (2006.01) |
| G01N 21/27 | (2006.01) |
| G01N 21/51 | (2006.01) |

(52) U.S. Cl.
CPC ...... G01N 21/4785 (2013.01); G01N 2021/513 (2013.01); G01N 21/53 (2013.01); G01N 21/51 (2013.01); G01N 21/274 (2013.01)
USPC .......................................................... 356/341

(58) Field of Classification Search
CPC ..................................................... G01N 21/00
USPC ................................................. 356/337, 341
See application file for complete search history.

(56) References Cited

U.S. PATENT DOCUMENTS

| 3,976,891 A | 8/1976 | Parkinson |
| 4,688,017 A * | 8/1987 | Huebner et al. ............... 341/137 |

(Continued)

FOREIGN PATENT DOCUMENTS

JP        10239237        9/1998

OTHER PUBLICATIONS

International Search Report, PCT International Application No. PCT/EP2011/050031, dated May 30, 2011.

(Continued)

*Primary Examiner* — Roy M Punnoose
(74) *Attorney, Agent, or Firm* — Kenyon & Kenyon LLP

(57) ABSTRACT

A method for determining the quality of the measuring results of a scattered light meter for measuring the particle concentration in motor vehicle exhaust gases, which has at least one scattered light measuring chamber, at least one light source and at least one light sensor, includes the steps: determining the difference between two scattered light sensor signals, that were picked up in a reference state of the scattered light meter; determining the difference between two scattered light sensor signals, which were picked up in a used state of the scattered light meter; and comparing the difference of the signals picked up in the used state to the reference signal difference of the signals picked up in the reference state.

18 Claims, 1 Drawing Sheet

(56) References Cited

U.S. PATENT DOCUMENTS

| | | | |
|---|---|---|---|
| 5,467,187 A | | 11/1995 | Beers |
| 6,315,955 B1 | * | 11/2001 | Klein .............................. 422/73 |
| 2009/0075248 A1 | | 3/2009 | Debreczeny et al. |
| 2010/0284917 A1 | * | 11/2010 | Kustner et al. ................. 424/9.1 |

OTHER PUBLICATIONS

Casella Cel, "MICRODUST pro Aerosol Monitoring System WINDUST pro Application Software Users Handbook—HB3275-06," <http://www.bgiusa.com/iq/microdust_hb_i6.pdf>, 2003.

* cited by examiner

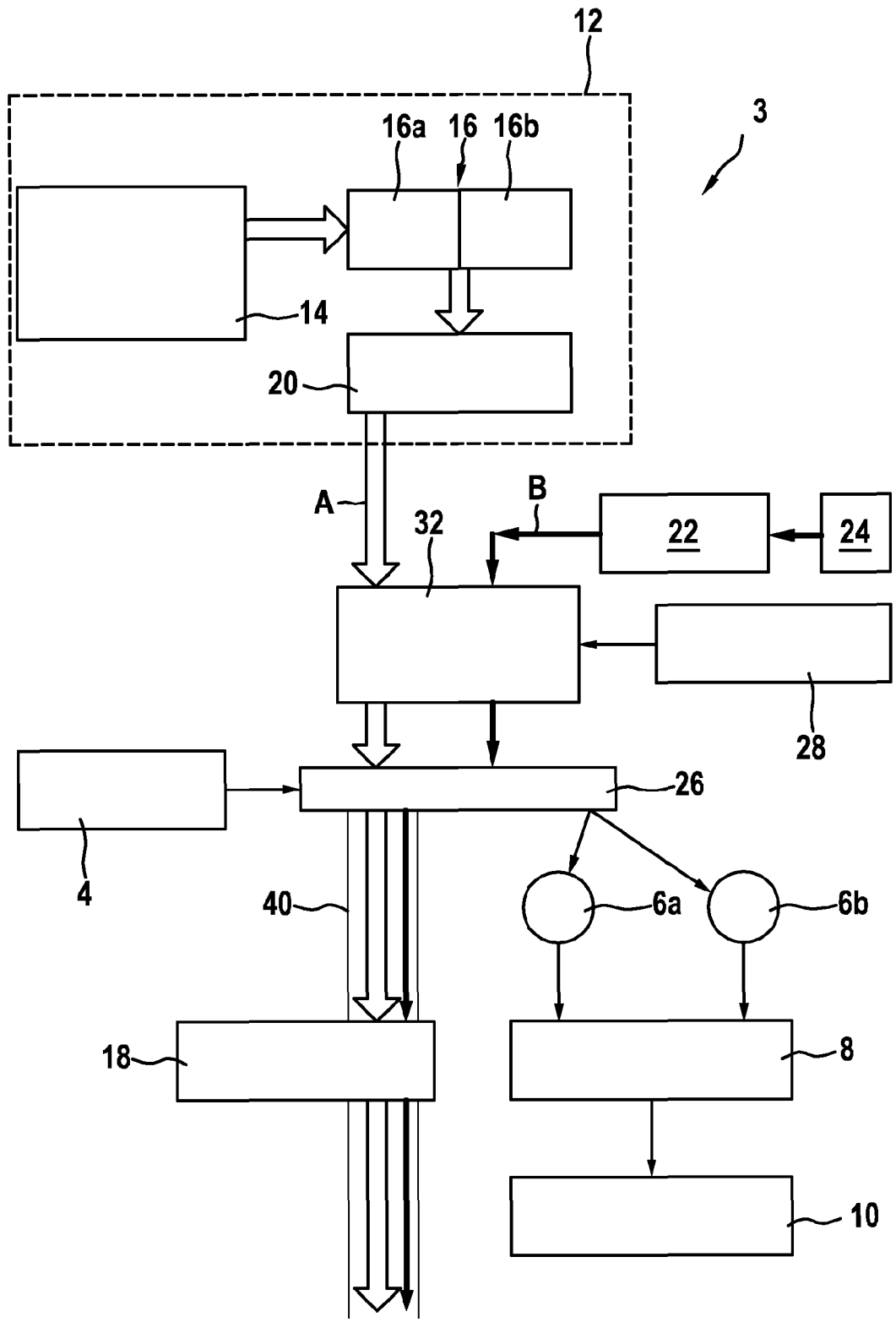

METHOD AND DEVICE FOR DETERMINING THE QUALITY OF MEASUREMENT RESULTS OF A SCATTERED LIGHT METER

FIELD OF THE INVENTION

The present invention relates to methods for determining the quality of the measuring results of a scattered light meter, as is used for measuring particle concentrations in motor vehicle exhaust gases and a scattered light meter which is developed for carrying out a method according to the present invention.

BACKGROUND INFORMATION

Conventionally, scattered light methods are used for measuring the concentration of particles in exhaust gases and other colloids.

In this context, an intense light source, such as a laser, situated in a measurement chamber, is usually used, and the colloid to be measured is guided through the measurement chamber. In the measuring chamber, there is at least one light sensor which detects scattered light, that has been scattered by the particulates present in the colloid. Even when so-called purge air curtains are used in order to keep the light output areas of the light sources and the light input areas of the light sensors, that come into contact with the exhaust gases, free of deposits, the light input areas and the light output areas become soiled, in the course of time, by deposits of particulates, the intensity of the signals emitted by the light sensors decreases and the measuring results are corrupted. A corruption of measuring results may also be caused by the aging of components of the light source, of the light sensors and/or the amplification electronics and evaluation electronics.

It is therefore important to detect soling and/or aging of the critical components of such a meter, in order to assess the accuracy and the validity of the data measured by using the meter.

Exhaust gas measuring instruments, that are used for official measurements, are covered by official calibration duty, whereby the necessity for assuring sufficient accuracy of the measurement results increases even further.

SUMMARY

One object of the present invention is to determine reliably, and at good accuracy, the quality of the measuring results of a scattered light meter.

An example method according to the present invention for determining the quality of the measuring results of a scattered light meter, which is provided for measuring a particle concentration in motor vehicle exhaust gases, and has at least one light source and at least one light sensor, includes the step of operating the scattered light meter first in a defined reference state, in which ideally no deposits are present in the scattered light measuring chamber, and the components are present in a new value state (initialization). This state exists, for example, directly after the manufacture of the scattered light meter and after the exchange or the thorough cleaning of the relevant components, such as the scattered light measuring chamber.

According to the present invention, the scattered light meter, which exists in a described reference state, is operated in a first specified operating state. In a first variant, the light source is switched off in a first operating state. Alternatively, the light source is switched on in a first operating state, and a first reference gas flow, having a first specified particle concentration, or a first measuring body having specified scattering properties is introduced into the scattered light measuring chamber, so as to generate specified scattered light. The signal of one or more scattered light sensors is measured and stored as first scattered light sensor signal S1.

The scattered light meter is put into a second specified operating state, in which the light source is switched on, and a second reference gas flow having a second specified particle concentration or a second measuring body having specified scattering properties, which differ from the scattering properties of the first measuring body, is inserted into the scattered light measuring chamber, in order to generate specified scattered light which differs from the scattered light in the first operating state.

In the second specified operating state, too, the signal of the scattered light sensor or scattered light sensors is measured, and stored as second scattered light sensor signal S2.

The difference between the second scattered light sensor signal S2 and the first scattered light sensor signal S1 results in a reference signal difference R=S2−S1, which is stored in a suitable memory device for later use.

The initialization of the example method according to the present invention is finished after this is done.

For the determination of the quality of the measurement results, which has been in operation for a certain time and/or a certain number of measuring processes, the abovementioned steps are repeated.

The first specified operating state set up during the initialization, in which the light source is switched off or in which the light source is switched on, and a first reference gas flow having a first specified particle concentration or the first measuring body is inserted into the scattered light measuring chamber, is reproduced and a first scattered light sensor signal M1 of the scattered light sensor, or sensors, is measured and stored.

Thereafter, the second specified operating state set up during the initialization, in which a second reference gas flow, which has a second specified particle concentration, or the second measuring body inserted into the scattered light measuring chamber is set, and a second scattered light sensor signal M2 is measured and stored. The difference D=M2−M1 between scattered light sensor signals M2 and M1 measured in the two operating states is calculated and compared to the reference signal difference R determined in the initialization.

The deviation of the signal difference D, ascertained in the used, or rather aged state of the scattered light meter from reference signal difference R is a reliable measure of the quality of the measurement results of the scattered light meter.

For the deviation of signal difference D, ascertained in the used, or rather the aged state of the scattered light meter from reference signal difference R, a threshold value may be specified, at whose exceeding a warning is indicated, and/or the further operation of the scattered light meter is prevented, since the accuracy of the results no longer corresponds to the (legal) requirements. Two threshold values may also be specified in such a way that, in response to the exceeding of a first, lower threshold value a warning is output, and upon the exceeding of a second, higher threshold value, the further operation of the scattered light meter is prevented.

Because the example method is based on the comparison of the differences of two scattered light sensor signals in each case, which have been recorded in two different operating states, systemic errors, such as offset errors of the sensor system and the amplification device may be excluded or at least reduced. The method thereby achieves a particularly great accuracy.

In one specific embodiment, the light source is switched off in the first specified operating state, and the dark value of the scattered light measuring chamber, that is, the output signal of the scattered light sensor, which is output at switched-off light source and dark measuring chamber, is used as scattered light sensor signal S1. In this specific embodiment, only a single reference gas flow having a specified particle concentration has to be provided. The method is therefore particularly simple and cost-effective to carry out.

In one alternative specific embodiment of the method according to the present invention, the light source in both specified operating states is switched on, and in each operating state, a reference gas flow having a specified particle concentration is guided through the scattered light measuring chamber, the particle concentration in the second operating state differing from the particle concentration in the first operating state. By such a method, in which two reference gas flows, having different particle concentrations, are compared to each other, the degree of soiling is able to be determined with a particularly high accuracy.

In one specific embodiment, one of the reference gases is a so-called null gas, that is, a gas having a particularly low particle concentration. Such a null gas is frequently available as scavenging gas and/or as gas for the zero calibration of the meter. The method is therefore able to be carried out cost-effectively, without additional expenditure, using the present null gas, for providing a reference gas.

In one specific embodiment, in at least one operating state, a measuring body, which scatters irradiated light in a specified manner, is inserted into the measuring chamber. The measuring body is designed so that it simulates the scattering behavior of a reference gas flow with a specified particle concentration. Since such a measuring body is not subject to a noticeable aging process, and therefore has a scattering behavior that is constant over a long time, by using such a measuring body, a specified operating state is able to be repeated and set permanently, particularly effectively and simply, at high accuracy and reproducibility.

In one specific embodiment of the method, the steps for determining the quality of the measurement results are carried out regularly, at specified time intervals. Thereby it is assured that the quality of the measurement results of the scattered light meter is regularly monitored and soiling and/or aging of the components, which could impair the measuring results negatively, are detected in good time.

In one specific embodiment, the steps for determining the quality of the measurement results are carried out regularly, according to a specified number of measuring processes. Thereby, the quality of the measurement results is reliably monitored, even during heavy use of the meter, at which monitoring at specified time intervals is not sufficient. If the meter is used only rarely, because of such a method, superfluous checking, which requires time in which the unit is not available for measurements, may be saved.

The two example methods may also be combined in such a way that checking the quality of the measurement results always takes place when a specified number of measurement processes has been carried out or when a specified time has passed since the last checking, whichever criterion is reached first. By such a combination, the measurement accuracy of the meter may be permanently ensured at the least possible expenditure, under the most varied operating conditions of the meter.

In one specific embodiment of the method, the results of all monitoring is permanently stored. Thus, the soiling and aging of the meter are protocoled over its entire service life, and may be utilized for calibrating, monitoring and/or maintenance purposes.

In one specific embodiment of the method, the initialization steps for determining the reference state are undertaken immediately after the production of the scattered light meter. In this state, the measuring chamber is not soiled, and the other components are also in a new value state, so that the reference state is able to be ascertained particularly accurately. Also, the initialization may be done by the manufacturer, without having to burden the user with it, and it is prevented that inexperienced users forget the initialization or carry it out in a faulty manner.

Alternatively, the initialization may be undertaken directly after setting up the scattered light meter at the location of use. In addition, the initialization may also be undertaken after cleaning the scattered light measurement chamber and/or after the exchange of components relevant to the measurement accuracy, in order to obtain a current reference value in each case.

The present invention also includes a scattered light meter, for measuring the particle concentration in motor vehicle exhaust gases, having at least one storage device for storing the reference signal difference, and a control device that is developed to control the scattered light meter in such a way that it carries out a method according to the present invention.

The present invention is explained in detail below, with reference to the FIGURE.

BRIEF DESCRIPTION OF THE DRAWING

The FIGURE shows schematically an exemplary embodiment of a scattered light measuring device for carrying out an example method according to the present invention.

DETAILED DESCRIPTION OF EXAMPLE EMBODIMENTS

The scattered light measuring device 3 shown in the FIGURE has a measuring chamber 26 having a light source 4, which, for instance, is developed as a laser, and which radiates light into measuring chamber 26 during operation. In measuring chamber 26, two light sensors 6a, 6b are situated. In the schematic representation of FIG. 1, light sensors 6a, 6b, for reasons of greater clarity, are drawn outside measuring chamber 26, although, in reality, they are at least partially situated within or on measuring chamber 26. Light sensors 6a, 6b record light radiated by light source 4, after it has been scattered by particles present in measuring chamber 26. Light source 4 and light sensors 6a, 6b are situated so that no light radiates directly from light source 4 onto, or into light sensors 6a, 6b. Light sensors 6a, 6b are preferably situated in such a way that light, which is scattered by the particles at various angles, is recorded by different light sensors 6a, 6b.

Light sensors 6a, 6b are electrically connected to an evaluation unit 8, which evaluates the signals emitted by light sensors 6a, 6b and which, in particular, determines the particle concentration of the colloid in measuring chamber 26 from the signals emitted by light sensors 6a, 6b. The results of the evaluation are output via an output device 10. Output device 10 may include a display, a printer and/or a data interface which is developed to transmit the results to a data processing device or a data storage device, such as a disk or a USB stick.

The exhaust gases to be measured, of a schematically shown motor vehicle 24, are picked up by an exhaust gas probe 22, which is situated in or at the exhaust of motor vehicle 24, and are guided by an exhaust gas hose and switching element 32 to measuring chamber 26. (Exhaust gas flow B).

Switching element 32 is functionally linked to a control unit 28 and may be switched over between an open state, in which it admits an inflow of exhaust gases from motor vehicle 24 into measuring chamber 26, and a closed state, in which the inflow of exhaust gases from motor vehicle 24 into measuring chamber 26 is switched off. Control unit 28 is connected, for instance, electrically or hydraulically to switching element 32, which may be developed as a valve, for example.

From measuring chamber 26, the exhaust gases flow outwards, via an exhaust gas removal device 40, without soiling or poisoning the direct surroundings of measuring chamber 26, such as the workshop or the measuring location.

One scattered light measuring device 3, according to the present invention, additionally has a null gas source 12, which provides so-called null gas, i.e., gas having a particularly low particle concentration. Null gas source 12 has an air feed 14, which takes up air from the surroundings. If scattered light measuring device 3 is being operated in a particularly soiled and/or dust-containing surroundings, such as in a workshop, air feed 14 may be developed as a pipe or chimney, which brings in the surrounding air from a greater distance, such as from outside the building. Alternatively, particularly clean air may also be taken from delivered gas cylinders.

Air feed 14 supplies the surrounding air taken up to a filtering unit 16, which is developed to reduce the particle concentration in the air taken up. For this, filtering unit 16 has at least one fine filter 16 (e.g. a so-called HEPA filter), which is in a position to filter the air supplied in such a way that the level of the signal strength generated by light sensors 6a, 6b, which was caused by those particles which are still contained in the null gas even after the filtering, is reduced to a value that is lower than the value that is ascertained at particle concentrations in exhaust gases of vehicles having a well functioning particulate filter present.

A coarse filter 16a is preconnected to the fine filter, which filters out particularly coarse particles from the air supplied, before they get to fine filter 16b. This avoids a rapid soiling and/or clogging of fine filter 16b by coarse particles, and the maintenance intervals for replacing or cleaning filters 16a, 16b are able to be prolonged. Coarse filter 16a and fine filter 16b, depending on the respective degree of soiling, may be replaced or cleaned separately, so as to reduce the maintenance costs.

A pump 18 for conveying the null gas is provided downstream from measuring chamber 26. Pump 18 conveys the null gas from null gas source 12 by suctioning the null gas through measuring chamber 26. At the same time, pump 18, when it is also being operated during the measuring process, supports exhaust gas flow B from motor vehicle 24 through measuring chamber 26.

In one alternative exemplary embodiment not shown, pump 18 is situated upstream of measuring chamber 26 in null gas flow A and/or exhaust gas flow B.

During the course of the null gas flow between air supply 14 and measuring chamber 26, a pressure sensor 20 is provided, which measures the pressure of the null gas supplied and passes on the result to a control unit not shown in FIG. 1. The pressure measured by pressure sensor 20 may be used for the regulation of pump 18, in order continuously to ensure a sufficient null gas flow through measuring chamber 26.

If the performance of pump 18 is known, one may draw a conclusion on the soiling of filter unit 16, since a large pressure drop takes place over a greatly soiled filter unit 16. If the pressure drop over filter unit 16 exceeds a specified boundary value, a warning signal may be emitted which points out to the user that at least one of filters 16a, 16b of filter unit 16 should be replaced. Pump 18 may also be switched off upon the exceeding of a second, higher boundary value, if the soiling of the filter is so great that certain functioning of null gas source 12 is no longer assured, or if there is the danger that pump 18 will be overloaded and/or damaged.

Alternatively or in addition, a pressure sensor 20 may be situated upstream of filter unit 16, in order to measure the pressure of the null gas before filter unit 16.

In a reference state of scattered light measuring device 3, for instance, directly after its manufacture or delivery, a reference signal difference R is ascertained.

A so-called zero calibration is carried out before the actual measuring process.

Pump 18 of null gas source 12 is switched on, so that null gas filtered by filter unit 16 flows from null gas source 12 into measuring chamber 26.

Light source 4 is switched on and the signals emitted by light sensors 6a, 6b, which are based on scattered light, which is scattered by particles which are present in the null gas guided into measuring chamber 26 and has been detected by light sensors 6a, 6b, are evaluated in order to define the null state of scattered light measuring device 3.

After the zero calibration has been carried out, control unit 28 controls switch element 32 in such a way that the supply of exhaust gases by motor vehicle 24 to measuring chamber 26 is opened, and exhaust gases flow from motor vehicle 24 (exhaust gas flow B), so that the particle concentration in the exhaust gases flowing through the measuring chamber is able to be measured.

In the exemplary embodiment shown in the FIGURE, null gas flow A is not switched off during the measurement of the particle concentration in the exhaust gases of motor vehicle 24. Rather, the null gas from null gas source 12 flows through measuring chamber 26 simultaneously with the exhaust gases to be measured. In this context, the null gas is guided along, for instance, as scavenging gas directly before sensors 6a, 6b and/or the light exit opening of light source 4, in order to prevent, or at least minimize the soiling of sensors 6a, 6b or the light exit opening by the deposition of particles from exhaust gas flow B.

In an alternative exemplary embodiment not shown, null gas flow A is switched off during the measurement, in order to avoid the dilution of exhaust gas flow B by null gas.

The invention claimed is:

1. A method for determining the quality of measuring results of a scattered light meter, which is provided for measuring particle concentration in motor vehicle exhaust gases, and has at least one scattered light measuring chamber, at least one light source and at least one light sensor, the method comprising:
   A) in a reference state of the scattered light meter:
      A1) measuring and storing a first scattered light sensor signal in a first specified operating state of the scattered light meter;
      A2) measuring and storing a second scattered light sensor signal in a second specified operating state of the scattered light meter;
      A3) ascertaining and storing a reference signal difference between the second scattered light sensor signal and the first scattered light sensor signal;
   B) in a used state of the scattered light meter:
      B1) measuring and storing a third scattered light sensor signal in the first specified operating state of the scattered light meter;

B2) measuring and storing a fourth scattered light sensor signal in the second specified operating state of the scattered light meter;
B3) ascertaining and storing a signal difference between the second scattered light sensor signal and the first scattered light sensor signal; and
C) comparing the signal difference in the used state to the reference signal difference picked up in the reference state.

2. The method as recited in claim 1, wherein the light source is switched off in the first specified operating state.

3. The method as recited in claim 1, wherein, in at least one of the operating states, a measuring body having a specified scattering behavior is inserted into the scattered light measuring chamber.

4. The method as recited in claim 1, wherein the light source is switched on in at least one of the operating states, and a reference gas flow having a specified particle concentration is guided through the scattered light measuring chamber.

5. The method as recited in claim 4, wherein a reference gas is a null gas having a low particle concentration.

6. The method as recited in claim 1, wherein steps B1 through B3 and C to be carried out in a used state of the scattered light meter are carried out regularly at at least one of specified time intervals, and after a specified number of measuring processes.

7. The method as recited in claim 1, wherein steps A1 through A3 are undertaken for ascertaining the reference signal difference directly after manufacture of the scattered light meter.

8. The method as recited in claim 1, wherein the steps A1 through A3 are undertaken for ascertaining the reference signal difference directly after setting up of the scattered light meter at its location of use.

9. The method as recited in claim 1, wherein the steps A1 through A3 are undertaken for ascertaining the reference signal difference after a cleaning of the scattered light measuring chamber.

10. A scattered light meter for determining a quality of the measuring particle concentration in motor vehicle exhaust gases, comprising:
a scattered light meter arrangement, for measuring the particle concentration in motor vehicle exhaust gases, having at least one scattered light measuring chamber, at least one light source and at least one light sensor, and at least one storage device for storing a reference signal difference; and
a control device, which is configured to perform the following:
A) in a reference state of the scattered light meter:
A1) measuring and storing a first scattered light sensor signal in a first specified operating state of the scattered light meter;
A2) measuring and storing a second scattered light sensor signal in a second specified operating state of the scattered light meter;
A3) ascertaining and storing a reference signal difference between the second scattered light sensor signal and the first scattered light sensor signal;
B) in a used state of the scattered light meter:
B1) measuring and storing a third scattered light sensor signal in the first specified operating state of the scattered light meter;
B2) measuring and storing a fourth scattered light sensor signal in the second specified operating state of the scattered light meter;
B3) ascertaining and storing a signal difference between the second scattered light sensor signal and the first scattered light sensor signal; and
C) comparing the signal difference in the used state to the reference signal difference picked up in the reference state.

11. The scattered light meter as recited in claim 10, wherein the light source is switched off in the first specified operating state.

12. The scattered light meter as recited in claim 10, wherein, in at least one of the operating states, a measuring body having a specified scattering behavior is inserted into the scattered light measuring chamber.

13. The scattered light meter as recited in claim 10, wherein the light source is switched on in at least one of the operating states, and a reference gas flow having a specified particle concentration is guided through the scattered light measuring chamber.

14. The scattered light meter as recited in claim 13, wherein a reference gas is a null gas having a low particle concentration.

15. The scattered light meter as recited in claim 10, wherein B1 through B3 and C to be carried out in a used state of the scattered light meter are carried out regularly at at least one of specified time intervals, and after a specified number of measuring processes.

16. The scattered light meter as recited in claim 10, wherein A1 through A3 are undertaken for ascertaining the reference signal difference directly after manufacture of the scattered light meter.

17. The scattered light meter as recited in claim 10, wherein A1 through A3 are undertaken for ascertaining the reference signal difference directly after setting up of the scattered light meter at its location of use.

18. The scattered light meter as recited in claim 10, wherein A1 through A3 are undertaken for ascertaining the reference signal difference after a cleaning of the scattered light measuring chamber.

* * * * *